United States Patent
Kuribara et al.

(10) Patent No.: US 7,663,103 B2
(45) Date of Patent: Feb. 16, 2010

(54) LINE-WIDTH MEASUREMENT ADJUSTING METHOD AND SCANNING ELECTRON MICROSCOPE

(75) Inventors: Masayuki Kuribara, Tokyo (JP); Jun Matsumoto, Tokyo (JP)

(73) Assignee: Advantest Corp., Tokyo (JP)

( * ) Notice: Subject to any disclaimer, the term of this patent is extended or adjusted under 35 U.S.C. 154(b) by 362 days.

(21) Appl. No.: 11/726,966

(22) Filed: Mar. 23, 2007

(65) Prior Publication Data

US 2007/0284525 A1    Dec. 13, 2007

(30) Foreign Application Priority Data

Mar. 27, 2006  (JP) .............................. 2006-084868

(51) Int. Cl.
*G01N 23/225*  (2006.01)
(52) U.S. Cl. ..................... 250/310; 250/306; 250/307; 250/311; 850/8; 850/9; 850/10; 850/11
(58) Field of Classification Search ................ 250/306, 250/307, 310, 311; 850/8–11
See application file for complete search history.

(56) References Cited

U.S. PATENT DOCUMENTS 4,038,543 A * 7/1977 Krisch et al. ................ 250/307
5,750,990 A * 5/1998 Mizuno et al. ................. 850/9
6,476,388 B1 * 11/2002 Nakagaki et al. ............... 850/9
2001/0035495 A1 * 11/2001 Nagai et al. .................. 250/311

FOREIGN PATENT DOCUMENTS

JP    05-296754    11/1993
JP    09-184714    7/1997

* cited by examiner

*Primary Examiner*—David A Vanore
*Assistant Examiner*—Michael Maskell
(74) *Attorney, Agent, or Firm*—Muramatsu & Associates

(57) ABSTRACT

A line-width measurement adjusting method, which is used when first and second electron beam intensity distributions for measuring a line width are produced from intensity distribution images of secondary electrons obtained respectively by scanning a first irradiation distance with an electron beam at first magnification, and by scanning a second irradiation distance with an electron beam at second magnification, includes the step of adjusting the second electron beam intensity distribution of the electron beam at the second magnification such that the second electron beam intensity distribution is equal to the first electron beam intensity distribution of the electron beam at first magnification. The second electron beam intensity distribution may be adjusted by increasing or decreasing a second irradiation distance when producing the electron beam intensity distribution.

9 Claims, 14 Drawing Sheets

| IRRADIATION POINT | 1 | 2 | 3 | 4 | 5 | 6 | 7 | 8 | 9 |
|---|---|---|---|---|---|---|---|---|---|
| QUANTITY OF ELECTRON BEAM | 1 | 1 | 2 | 2 | 3 | 2 | 2 | 1 | 1 |

IRRADIATION POINT

| | (LEFT) | 1 | 2 | 6 | 8 | 7.5 | | | | |
|---|---|---|---|---|---|---|---|---|---|---|
| × QUANTITY OF ELECTRON BEAM | (RIGHT) | | | | | | 7.5 | 12 | 14 | 8 | 9 |

$X_{0L}$ = 3.27

$X_{0R}$ = 6.73

VALUE OF ELECTRON BEAM INTENSITY DISTRIBUTION = 6.73 − 3.27
= 3.46

FIG. 7A

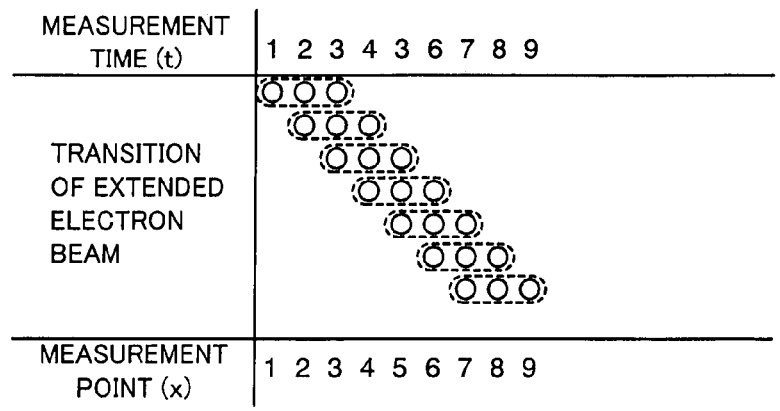

| MEASUREMENT TIME (t) | 1 2 3 4 3 6 7 8 9 |
|---|---|
| TRANSITION OF EXTENDED ELECTRON BEAM | |
| MEASUREMENT POINT (x) | 1 2 3 4 5 6 7 8 9 |

FIG. 7B

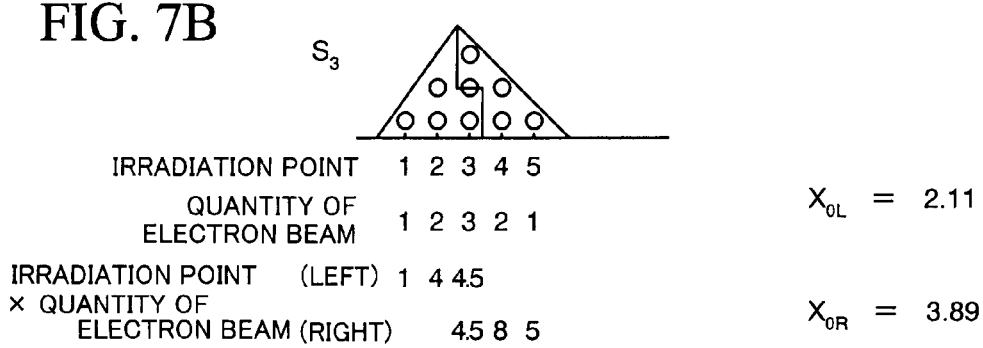

IRRADIATION POINT    1 2 3 4 5
QUANTITY OF ELECTRON BEAM    1 2 3 2 1

IRRADIATION POINT (LEFT)    1 4 4.5
× QUANTITY OF
ELECTRON BEAM (RIGHT)    4.5 8 5

$X_{0L}$ = 2.11

$X_{0R}$ = 3.89

VALUE OF ELECTRON BEAM INTENSITY DISTRIBUTION = 3.89-2.11
= <u>1.78</u>

FIG. 7C

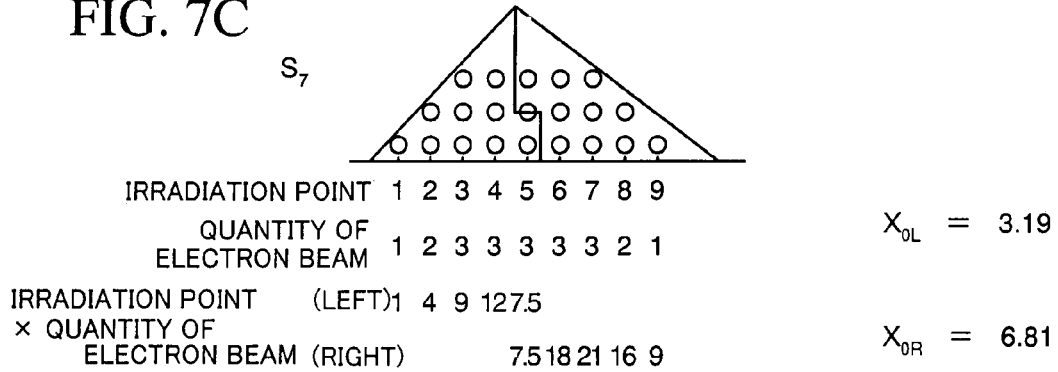

IRRADIATION POINT    1 2 3 4 5 6 7 8 9
QUANTITY OF ELECTRON BEAM    1 2 3 3 3 3 3 2 1

IRRADIATION POINT (LEFT)    1 4 9 12 7.5
× QUANTITY OF
ELECTRON BEAM (RIGHT)    7.5 18 21 16 9

$X_{0L}$ = 3.19

$X_{0R}$ = 6.81

VALUE OF ELECTRON BEAM INTENSITY DISTRIBUTION = 6.81-3.19
= <u>3.62</u>

FIG. 9A
| MEASUREMENT TIME (t) | 1 | 2 | 3 | 4 | 5 | 6 | 7 | 8 | 9 | 10 |
|---|---|---|---|---|---|---|---|---|---|---|
| TRANSITION OF EXTENDED ELECTRON BEAM | ○○○○○○ | ○○○○○○ | ○○○○○○ | ○○○○○○ | ○○○○○○ | ○○○○○○ | ○○○○○○ | ○○○○○○ | ○○○○○○ | ○○○○○○ |
| IRRADIATION POINT (x) | 1 2 3 4 5 6 7 8 9 10 11 12 13 14 15 16 17 18 19 20 21 22 23 24 |
FIG. 9B
$S_3$ 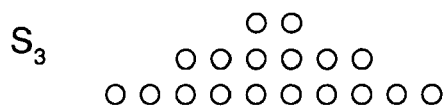
FIG. 9C
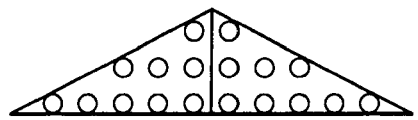
| IRRADIATION POINT | 1 | 2 | 3 | 4 | 5 | 6 | 7 | 8 | 9 | 10 |
|---|---|---|---|---|---|---|---|---|---|---|
| QUANTITY OF ELECTRON BEAM | 1 | 1 | 2 | 2 | 3 | 3 | 2 | 2 | 1 | 1 |
| IRRADIATION POINT × QUANTITY OF ELECTRON BEAM | 1 | 2 | 6 | 8 | 15 | 18 | 14 | 16 | 9 | 10 |
VALUE OF ELECTRON BEAM INTENSITY DISTRIBUTION  3.89

FIG. 10A
| MEASUREMENT TIME (t) | 1 | 2 | 3 | 4 | 5 | 6 | 7 | 8 | 9 | 10 |
|---|---|---|---|---|---|---|---|---|---|---|
| TRANSITION OF EXTENDED ELECTRON BEAM | ○ ○ ○ ○ ○ ○ ○ — C1 | | | | | | | | | |
| | | ○ ○ ○ ○ ○ ○ ○ — C2 | | | | | | | | |
| | | | ○ ○ ○ ○ ○ ○ ○ — C3 | | | | | | | |
| | | | | ○ ○ ○ ○ ○ ○ ○ | | | | | | |
| | | | | | ○ ○ ○ ○ ○ ○ ○ | | | | | |
| | | | | | | ○ ○ ○ ○ ○ ○ ○ | | | | |
| | | | | | | | ○ ○ ○ ○ ○ ○ ○ | | | |
| | | | | | | | | ○ ○ ○ ○ ○ ○ ○ | | |
| | | | | | | | | | ○ ○ ○ ○ ○ ○ ○ | |
| | | | | | | | | | | ○ ○ ○ ○ ○ ○ ○ |
| IRRADIATION POINT (x) | 1 2 3 4 5 6 7 8 9 10 11 12 13 14 15 16 17 18 19 20 21 22 23 24 25 | | | | | | | | | |
FIG. 10B
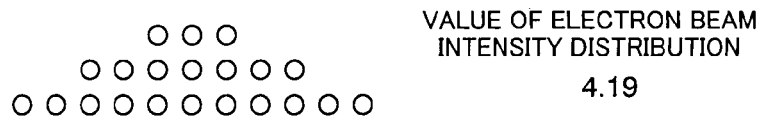
VALUE OF ELECTRON BEAM INTENSITY DISTRIBUTION
4.19
FIG. 10C
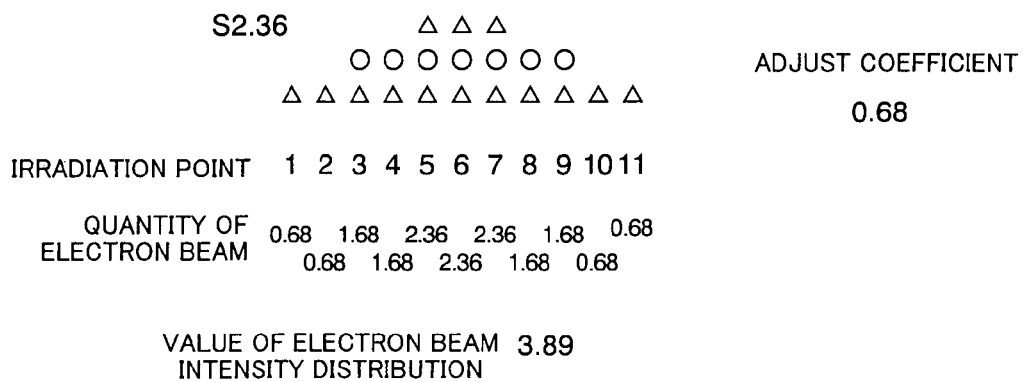
ADJUST COEFFICIENT
0.68
IRRADIATION POINT  1  2  3  4  5  6  7  8  9  10  11
QUANTITY OF ELECTRON BEAM  0.68  1.68  2.36  2.36  1.68  0.68
                                  0.68  1.68  2.36  1.68  0.68
VALUE OF ELECTRON BEAM INTENSITY DISTRIBUTION  3.89

FIG. 14A

| INITIAL MEASUREMENT POINT QUANTITY TABLE | |
|---|---|
| MAGNIFICATION | NUMBER OF MEASUREMENT POINTS |
| ×50k | 3.0 POINTS |
| ×75k | 4.5 POINTS |
| ×100k | 7.0 POINTS |

FIG. 14B

| OPERATIONAL MEASUREMENT POINT QUANTITY TABLE | |
|---|---|
| MAGNIFICATION | NUMBER OF MEASUREMENT POINTS |
| ×50k | 3.0 POINTS |
| ×75k | 4.5 POINTS |
| ×100k | 7.0 POINTS |

FIG. 14C

| STANDARD LINE WIDTH TABLE | |
|---|---|
| STANDARD MAGNIFICATION | ×50k |
| STANDARD LINE WIDTH Wr | 210nm | ns
LINE-WIDTH MEASUREMENT ADJUSTING METHOD AND SCANNING ELECTRON MICROSCOPE

CROSS-REFERENCE TO RELATED APPLICATIONS

This application is based on and claims priority of Japanese Patent Application No. 2006-084868 filed on Mar. 27, 2006, the entire contents of which are being incorporated herein by reference.

BACKGROUND OF THE INVENTION

1. Field of the Invention

The present invention relates to a line-width measurement adjusting method applicable to line-width measurement of a pattern using a scanning electron microscope, or more specifically to a line-width measurement adjusting method and a scanning electron microscope capable of avoiding fluctuation in a measured value when changing magnification.

2. Description of the Prior Art

Measurement using a scanning electron microscope has heretofore been applied to a line-width measuring method of a pattern. Here, a scanning electron microscope is configured to scan an electron beam scanning range by irradiating incident electrons, to acquire secondary electrons emitted from a sample by using a scintillator, to convert a quantity of electrons thus acquired into luminance, and to display a surface image of the sample on a display device.

In the case of managing characteristics of a semiconductor device with use of this scanning electron microscope, it is a general practice to check whether or not a line-width of a pattern is formed in the size within a design standard. The management of the pattern line-width is typically executed in accordance with the following procedures. After displaying a predetermined range of a resist pattern formed on a semiconductor wafer on a display device, an electron beam is focused and irradiated on a measurement point in the displayed range to acquire a waveform of luminance distribution based on secondary electrons reflected from the measurement point. Then, a high-level width in the waveform of luminance distribution is determined as a line width. A judgment is made as to whether or not this line width falls within an acceptable error range. If the line width is within the acceptable error range, a subsequent etching process is executed. In contrast, if the line width is out of the acceptable error range, the wafer is sent back to a process for forming the resist pattern.

In this way, the line-width measurement of the pattern is important in the manufacturing process of the semiconductor device, and various methods for accurately measuring the line width have been proposed. In general, a position where a slope of luminance corresponding to a quantity of secondary electrons becomes the maximum is defined as an edge position of the pattern.

Meanwhile, as another technique related thereto, Japanese Patent Application Laid-open Publication No. Hei 5 (1993)-296754 discloses an edge detection method of determining, as an edge position, a position where a secondary electron signal becomes the minimum.

As described above, the line-width measurement of the pattern with a scanning electron microscope employs the method of determining the position where the slope of luminance becomes the maximum as the edge position or the method of determining the position where the secondary electron signal becomes the minimum as the edge position.

Here, there are cases where measurement is performed by using the magnification of observation of different numbers of times, and where measurement is performed with the beam diameter of the electron beam in different size when a scanning direction or a measurement device is changed. These cases may cause a problem that different measurement results are obtained from the same measurement object.

When rescaling the magnification of observation, the measurement results may vary as follows. For example, use of the high magnification of observation causes an electron beam to travel in a short distance per unit time as compared to the case of use of the low magnification, whereby a range irradiated with the electron beam for a certain period of time is reduced. Generally, the detected edge position changes according to the size of the range irradiated with the electron beam, and this produces differences in the measurement result of the line width. For this reason, the measurement result of the line width varies between the case of high magnification of observation and the case of low magnification of observation.

Meanwhile, changes in the beam diameter causes the range irradiated with the electron beam to also vary. As similar to the case of resealing the magnification of observation, this also produces differences in the measurement result of the line width even when the same line width is measured.

In order to deal with these problems, a countermeasure has been taken heretofore in which the observation error is corrected by firstly acquiring correction data on the line width in each scale of the magnification of observation, and then by using the correlation in the correction data. Moreover, in the case of the changes in the beam diameter, the line width of the same sample is measured either in different scanning directions or with different measurement devices, and then beam diameter is readjusted when the measured values are different. However, it is troublesome to prevent the measurement results of the line width of the same pattern from varying, and difficult to execute the line-width measurement process efficiently.

SUMMARY OF THE INVENTION

The present invention has been made in light of the foregoing problems of the prior art. An object of the present invention is to provide a line-width measurement adjusting method for avoiding fluctuation in a measurement result when changing magnification of observation, a scanning direction or a measurement device, and to provide a scanning electron microscope having the line-width measurement adjusting method.

The above-mentioned problems are solved by providing a line-width measurement adjusting method, which is used when first and second electron beam intensity distributions for measuring a line width are produced from intensity distribution images of secondary electrons obtained respectively by scanning a first irradiation distance with an electron beam at first magnification, and by scanning a second irradiation distance with an electron beam at second magnification. Here, the method includes the step of adjusting second electron beam intensity distribution of the electron beam at the second magnification such that the second electron beam intensity distribution is equal to the first electron beam intensity distribution of the electron beam at the first magnification.

In the line-width measurement adjusting method of this aspect, the electron beam intensity distribution is expressed by an amount of electron beam per unit distance assuming that the amount of electron beam is measured for each unit distance in a scanning direction by scanning with the electron beam. Here, a value of the electron beam intensity distribution may be obtained by firstly dividing the electron beam intensity distribution in half in the scanning direction, that is, into a primary electron beam intensity distribution and a secondary electron beam intensity distribution, and by then finding a difference in distance between the center of mass of the first electron beam intensity distribution and the center of mass of the second electron beam intensity distribution. Meanwhile, the second electron beam intensity distribution may be adjusted by increasing or decreasing the second irradiation distance when producing the electron beam intensity distribution.

In the present invention, when the amounts of travel by scanning per unit time are different due to changing the magnification, the electron beam intensity distribution is adjusted so as to equalize the values of electron beam intensity distribution in terms of the respective amounts of travel each showing the distribution of the irradiated electron beam. In this way, the distances in the scanning direction of irradiation of the electron beams become almost equal even when the line-width is measured by resealing the magnification of observation. Accordingly, it is possible to prevent different measurement results of the line width.

Moreover, by adjusting the electron beam intensity distribution as described above, it is possible to obtain the value which is the same as that of measurement at high magnification of observation even when using low magnification of observation setting a wide range of a sample as a measurement target. In this way, it is possible to execute the line-width measurement efficiently in a wide range.

Meanwhile, the above-mentioned problems are resolved by providing a line-width measurement adjusting method using an intensity distribution image of secondary electrons obtained by scanning a first irradiation distance with an electron beam having a first beam diameter and an intensity distribution image of secondary electrons obtained by scanning a second irradiation distance with an electron beam having a second beam diameter. Here, the method includes the step of adjusting second electron beam intensity distribution of the electron beam having the second beam diameter when producing electron beam intensity distribution for measuring a line width such that first electron beam intensity distribution of the electron beam having the first beam diameter becomes equal to the second electron beam intensity distribution.

Furthermore, the above-mentioned problems are resolved by providing a line-width measurement adjusting method using an intensity distribution image of secondary electrons obtained by scanning a first irradiation distance with an electron beam configured to scan in a first direction and an intensity distribution image of secondary electrons obtained by scanning a second irradiation distance with an electron beam configured to scan in a second direction. Here, the method includes the step of adjusting second electron beam intensity distribution of the electron beam scanning in the second direction when producing electron beam intensity distribution for measuring a line width such that first electron beam intensity distribution of the electron beam scanning in the first direction equal to the second electron beam intensity distribution.

In the present invention, when the beam diameters of the electron beams are different due to use of different scanning electron microscopes, the distances of irradiation of the electron beams are equalized by adjusting the electron beam intensity distribution. Accordingly, it is possible to prevent different measurement results from arising between the scanning electron microscopes. Moreover, in the preset invention, when the shape of the electron beam is not a perfect circle and the beam diameter of the electron beam is different depending on the scanning direction, the distances irradiated with the electron beam are equalized by adjusting the electron beam intensity distribution depending on the scanning direction. Accordingly, it is possible to prevent different measurement results from arising depending on the scanning direction.

Additionally, another aspect of the present invention provides a scanning electron microscope that embodies the line-width measurement adjusting method according to the above-described aspects. An example of the scanning electron microscope of this aspect includes an electron gun for irradiating an electron beam onto a surface of a sample, an electron detection unit for detecting electrons emitted from the sample upon irradiation of the electron beam, and a control unit for adjusting second electron beam intensity distribution of the electron beam at second magnification such that first electron beam intensity distribution of the electron beam at first magnification becomes equal to the second electron beam intensity distribution.

BRIEF DESCRIPTION OF THE DRAWINGS

FIGS. 7A to 7C are second diagrams for explaining the electron beam intensity distribution adjusting process.

FIGS. 9A to 9C are third diagrams for explaining the electron beam intensity distribution adjusting process.

FIGS. 10A to 10C are fourth diagrams for explaining the electron beam intensity distribution adjusting process.

FIGS. 14A to 14C are charts showing examples of data used for the line-width measurement process.

DESCRIPTION OF THE PREFERRED EMBODIMENT

Now, a preferred embodiment of the present invention will be described with reference to the accompanying drawings.

A configuration of a scanning electron microscope will be described first. Then, a typical method of measuring a line width of a pattern will be described. Thereafter, an adjusting method for the line-width measurement in the case of changing magnification of observation or other factors will be described. Lastly, the line-width measurement using the line-width measurement adjusting method of the present invention will be described.

(Configuration of a Scanning Electron Microscope)

Figure 1:
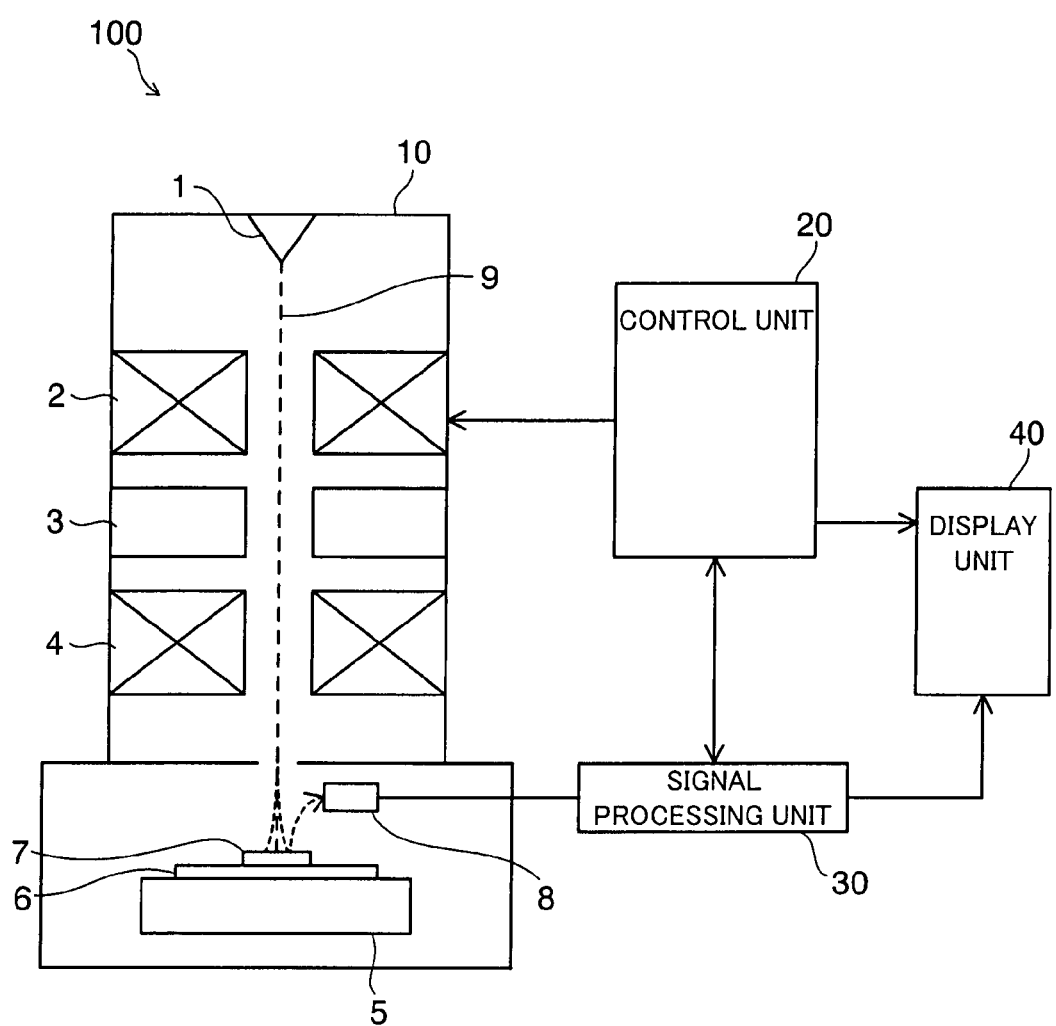
FIG. 1 is a block diagram of a scanning electron microscope used in an embodiment of the present invention.

FIG. 1 is a block diagram of a scanning electron microscope according to an embodiment of the present invention.

This scanning electron microscope 100 essentially includes an electron scanning unit 10, a signal processing unit 30, an image display unit 40, and a control unit 20 for controlling the electron scanning unit 10, the signal processing unit 30, and the image display unit 40. The electron scanning unit 10 includes an electron gun 1, a condenser lens 2, a deflecting coil 3, an object lens 4, a motion stage 5, and a sample holder 6.

Charged particles 9 are emitted from the electron gun 1 and irradiated onto a sample 7 on the motion stage 5 through the condenser lens 2, the deflecting coil 3, and the object lens 4.

A quantity of secondary electrons or reflected electrons coming out of the sample 7 upon irradiation of the charged particles 9 is detected by an electron detector 8 formed of a scintillator, for example, and the detected quantity is converted into a digital amount by an AD converter and further into a luminance signal used for display on the image display unit 40.

An electron deflection amount by the deflecting coil 3 and an image scanning amount by the image display unit 40 are controlled by the control unit 20. Meanwhile, the control unit 20 stores a program for executing line-width measurement.

(Typical Method of Measuring Line Width of Pattern)

Next, a typical method of measuring a line width of a pattern on a sample shown in FIG. 2A by use of the scanning electron microscope 100 illustrated in FIG. 1 will be described.

Figure 2A:
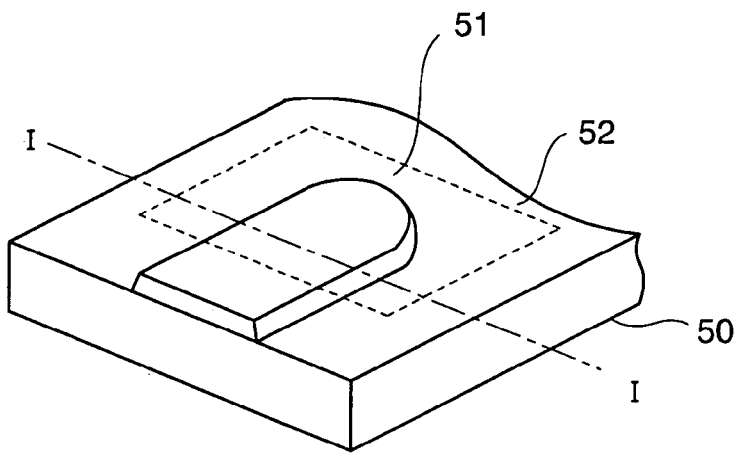
FIGS. 2A to 2C are diagrams for explaining an electron image and a profile to be acquired by a signal processing unit.

As shown in FIG. 2A, the sample 7 used herein includes a foundation layer 50 formed on a semiconductor wafer, and a line pattern 51 formed on the foundation layer 50. This line pattern 51 is a pattern targeted for dimensional management. Part of the sample 7 is formed into a planar shape as shown in FIG. 2A. Here, a portion surrounded by a broken line 52 indicates an observation area of the scanning electron microscope 100.

Figure 2B:
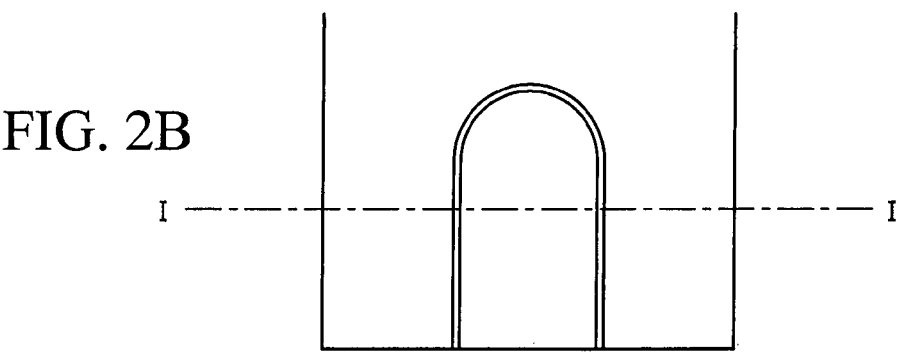

FIG. 2B shows an example of an image display, which is achieved by detecting the quantity of electrons such as secondary electrons with the electron detector by scanning the sample with an electron beam shown in FIG. 2A, converting the detected quantity of electrons into the luminance signal, and forming the image display by synchronizing the electron beam scanning and CRT scanning.

Figure 2C:
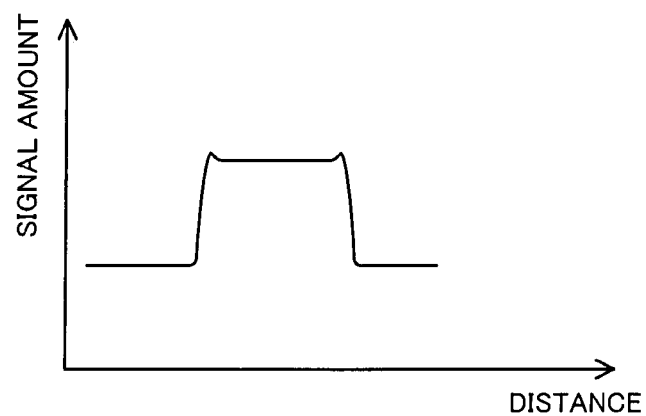

FIG. 2C is a view showing the quantity of electrons emitted from or reflected by the sample obtained at the time of irradiating the electron beam along the I-I line in FIG. 2A.

The quantity of electrons such as secondary electrons emitted from the sample upon irradiation of the electron beam varies depending on a surface condition of the sample. When the electron beam is irradiated perpendicularly to the sample, the quantity of emitted electrons is low if the sample has a flat surface. If the surface of the sample is inclined, the secondary electrons emitted laterally from a lower side of a slope travel for a short distance inside the sample. Accordingly, the amount of emitted electrons is increased as compared to the case of the flat surface. Moreover, the quantity of emitted or reflected electrons varies depending on the material on which the electron beam is irradiated.

As shown in FIG. 2C, a signal amount converted into luminance is low in a flat surface area where no line patterns are formed. In contrast, the signal amount is increased in an area where the line pattern is formed. Moreover, there is a large change in the signal amount at a boundary (an edge) between the area where no line patterns are formed and the area where the line pattern is formed. A line width is measured by calculating such edge positions.

As described above, the surface condition of the sample is observed by scanning the sample with the electron beam and calculating the condition by use of the quantity of electrons such as secondary electrons emitted from the surface of the sample. An electron microscopic image representing the surface condition varies depending on the point on the sample for which the quantity of electrons is used for calculation. For example, it is possible to express the surface condition more accurately in the case of a narrow interval between the points on the surface for acquiring the quantities of electrons such as secondary electrons as compared to the case of a wider interval. The point for acquiring the quantity of electrons such as secondary electrons is called as a measurement point. When magnification of observation is high, the electron beam scans a narrower range as compared to a case where the magnification of observation is low. This is due to the fact that the electron beam scans the narrower range in the case of the high magnification of observation as compared to the case of the lower magnification of observation. However, a scanning time remains the same.

Meanwhile, there is also a case of using not only the quantity of electrons such as secondary electrons at a certain measurement point x but also the quantity of electrons such as secondary electrons at an adjacent measurement point as the value for indicating the surface condition of the sample. In this case, an average of the values on these measurement points is calculated and defined as the value for indicating the surface condition of the sample at the measurement point x. In this way, the value for indicating the surface condition of the sample is smoothed.

(Adjusting Method for Line-Width Measurement when Changing Magnification of Observation and Other Factors)

Next, an adjusting method for line-width measurement to equalize the measurement result of the same pattern in the case of changing magnification of observation will be described.

Figure 3A:
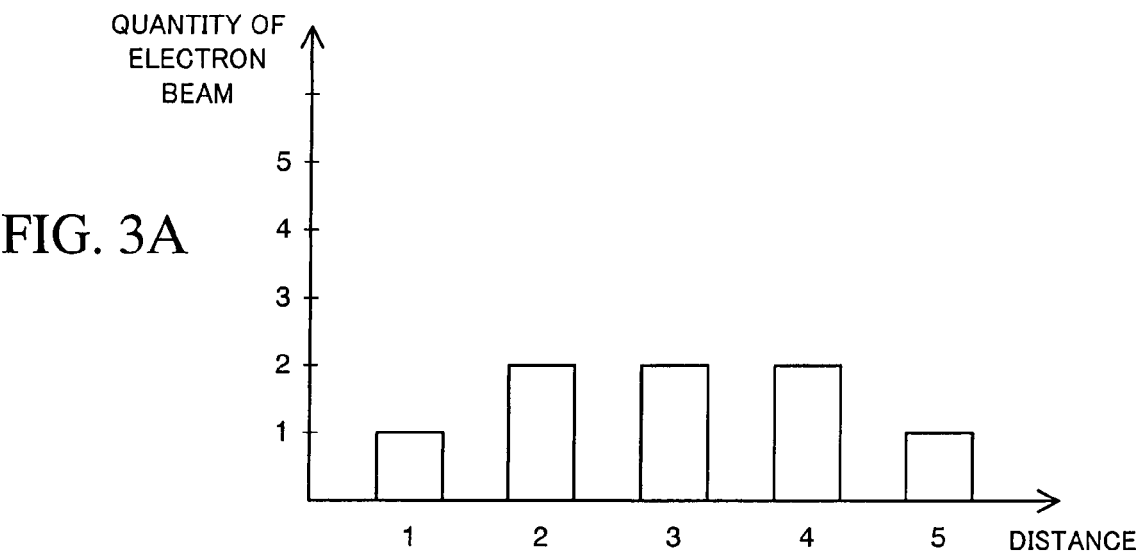
FIGS. 3A and 3B are graphs showing examples of electron beam intensity distribution.
Figure 3B:
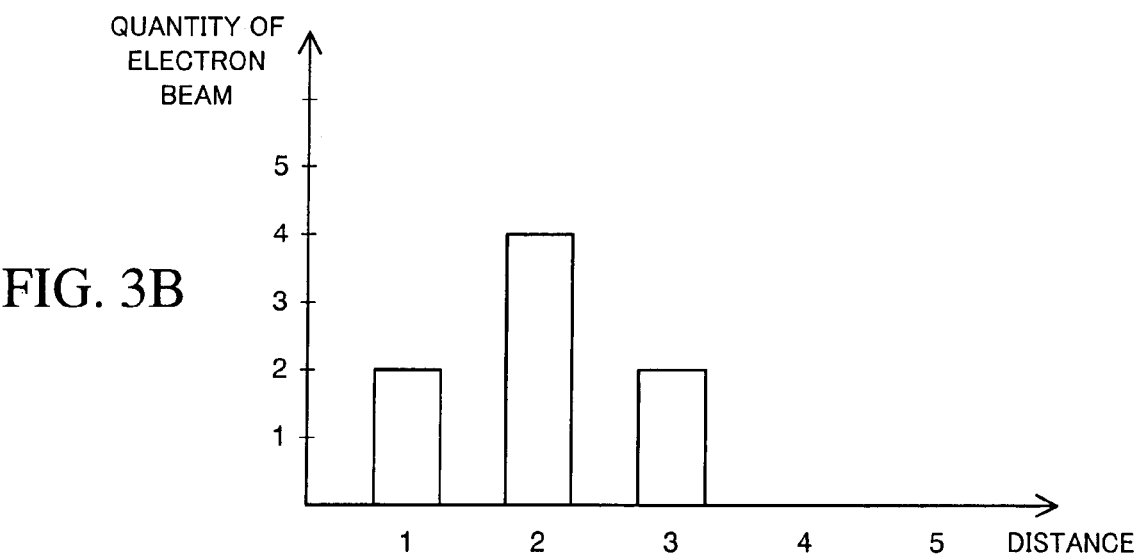

FIGS. 3A and 3B show electron beam intensity distribution obtained by electron beam scanning while setting two different values of magnification. The electron beam intensity distribution is expressed by an amount of electron beam per unit distance assuming that the amount of electron beam is measured for each unit distance in a scanning direction by scanning with the electron beam. For example, FIG. 3A shows the electron beam intensity distribution showing the amount of electron beam per unit distance when setting the distance in the scanning direction for irradiating the electron beam equal to 5. Meanwhile, FIG. 3B shows the electron beam intensity distribution showing the amount of electron beam per unit distance when setting the distance in the scanning direction for irradiating the electron beam equal to 3.

Here, FIG. 3A shows the example where the magnification of observation is set lower than the case in FIG. 3B, and a scanning time period is set equal between the case in FIG. 3A and the case in FIG. 3B. As shown in FIGS. 3A and 3B, the distance in the scanning direction for irradiating the electron beam is determined by the magnification of observation and the scanning time period. Even if the scanning time period is set constant, the scanning distance is different when resealing the magnification of observation. For this reason, the amounts of secondary electrons emitted from the sample beam are different when irradiating the electron beam for two different scanning distances. Consequently, the measurement result changes in spite of the same pattern.

In this embodiment, the electron beam intensity distribution in the case of scanning a predetermined distance is obtained respectively in terms of the magnification of observation as a standard and in terms of the magnification of observation different from the standard, and the electron beam intensity distribution obtained at the magnification of observation different from the standard is adjusted equal to the electron beam intensity distribution obtained at the standard magnification of observation. The adjustment of the electron beam intensity distribution obtained at the magnification of observation different from the standard is achieved by increasing or decreasing an irradiation surface distance of the electron beam (distance across the sample surface) from an image obtained by scanning the predetermined distance at the magnification of observation different from the standard when producing the electron beam intensity distribution. In this way, the distance in the scanning direction of the electron beam irradiation is set equal when the magnification of observation is different.

For example, when the electron beam intensity distribution shown in FIG. 3A is defined as the standard, the electron beam intensity distribution shown in FIG. 3B is adjusted to form the distribution equal to the electron beam intensity distribution shown in FIG. 3A. In this adjustment, the scanning distance in FIG. 3B is changed such that the distance of irradiation of the electron beam in the scanning direction therein becomes an approximate value to the distance in FIG. 3A.

A judgment as to whether or not the two types of the electron beam intensity distribution are equal is made by comparing the values representing the respective types of the electron beam intensity distribution. The value representing the electron beam intensity distribution is defined by dividing the electron beam intensity distribution in half along the scanning direction, calculating the center of mass for each of segments of the distribution divided in half, and finding a difference in distance between the centers of mass thus calculated.

Now, quantification of the electron beam intensity distribution will be described below with reference to FIGS. 4A and 4B.

Figure 4A:
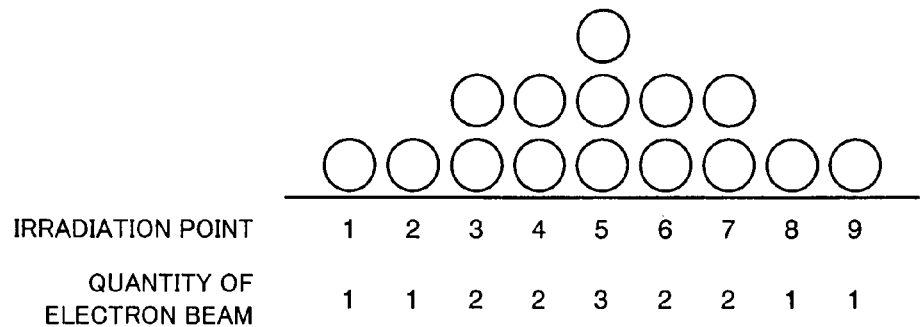
FIGS. 4A and 4B are diagrams showing a process to find a value of the electron beam intensity distribution.

FIG. 4A shows an example of the electron beam intensity distribution, in which the amount of electron beam of the measurement point located per unit distance is expressed in the number of unit electron beam amounts (indicated with circles). The electron beam intensity distribution in FIG. 4A has a spread of coordinates of the irradiation points (coordinates in the scanning direction) ranging from 1 to 9. Here, the amount of electron beam at the irradiation point 3 is equal to 2, for example.

Figure 4B:
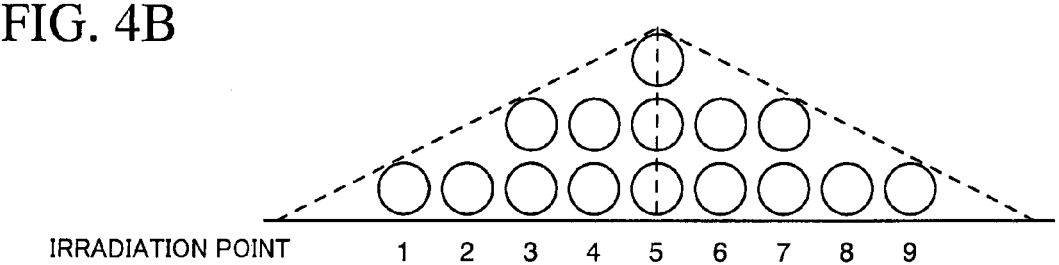

First, the electron beam intensity distribution shown in FIG. 4A is divided in half into a former half distribution segment and a latter half distribution segment along the scanning direction of the electron beam as shown in FIG. 4B. In FIG. 4B, the former half distribution segment ranges from 5 to 9 on the coordinate axis and the latter half distribution, segment ranges from 1 to 5 on the coordinate axis.

Next, regarding the electron beam intensity distribution shown in FIG. 4B, the former half distribution segment and the latter half distribution segment are respectively quantified.

The value of the former distribution segment is calculated by defining a multiplied value of the coordinate value in the scanning direction indicating the irradiation point of the electron beam and a total value of the unit electron beam irradiated on that irradiation point as the quantity of electron beam at that irradiation point and then dividing a sum of the quantities of electron beam in the respective irradiation points in the former distribution segment by a total of the unit electron beam amounts irradiated in the former distribution segment. Similarly, the value of the latter distribution segment is calculated by defining the multiplied value of the coordinate value in the scanning direction indicating the irradiation point of the electron beam and the total value of the unit electron beam irradiated on that irradiation point as the quantity of electron beam at that irradiation point and then dividing a sum of the quantities of electron beam in the respective irradiation points in the latter distribution segment by a total of the unit electron beam amounts irradiated in the latter distribution segment.

In this way, the values of the former distribution segment and the latter distribution segment indicate positions of the centers of mass on the coordinate axis in the scanning direction of the respective distribution segments, which are expressed by the following formula:

$$X_0 = \Sigma(X_i \times P_i)/\Sigma P_i$$

Here, $X_0$ is the center of mass, $X_i$ is the irradiation point per unit distance, and $P_i$ is the quantity of electron beam irradiated on the irradiation point $X_i$.

As a result of this calculation, as shown in FIG. 4B, the difference in distance between the center of mass ($X_{0R}$) of the former distribution segment and the center of mass ($X_{0L}$) of the latter distribution segment in the electron beam intensity distribution is equal to 3.46.

In this specification, the difference in distance between the center of mass of the former distribution segment and the center of mass of the latter distribution segment in the electron beam intensity distribution will also be referred to as an effective irradiation travel distance.

EXAMPLE 1

Next, a method of equalizing the electron beam intensity distribution at two different values of magnification of observation will be described.

First, calculation of the electron beam intensity distribution will be described with reference to FIG. 5A to FIG. 6B. Then, adjustment of the electron beam intensity distribution will be described with reference to FIG. 6A to FIG. 8.

(1) Calculation of Electron Beam Intensity Distribution

When the electron beam travels, the electron beam is irradiated in the size determined by a beam diameter. Accordingly, it is not possible to detect only the secondary electrons emitted by the electron beam irradiated on the measurement point x on the surface of the sample. The electron beam is also irradiated on a portion ahead of the measurement point x in the scanning direction. As a result, the secondary electrons emitted by the electron beam irradiated on the portion ahead in the scanning direction are also detected. In this way, the electron beam has a certain spread from the measurement point toward the scanning direction. For this reason, the quantity of electrons at the measurement point includes not only the quantity of electrons obtained from the measurement point but also the quantity of electrons obtained from the spread range of the electron beam.

Figure 5A:
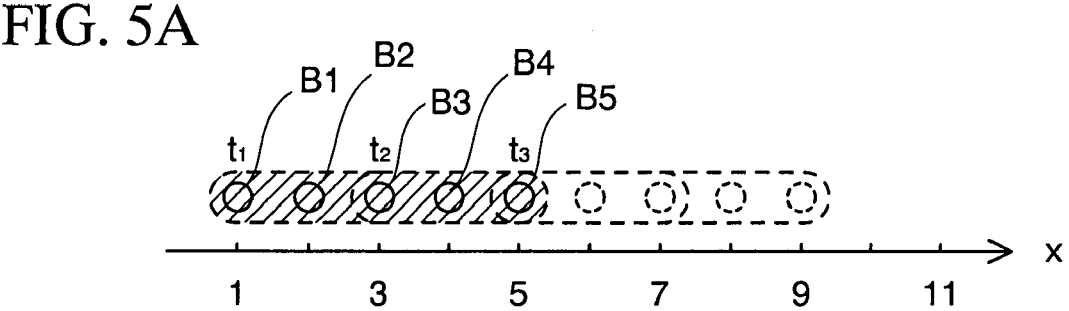
FIGS. 5A and 5B are diagrams for explaining an irradiated electron beam spreading in a scanning direction.
Figure 5B:
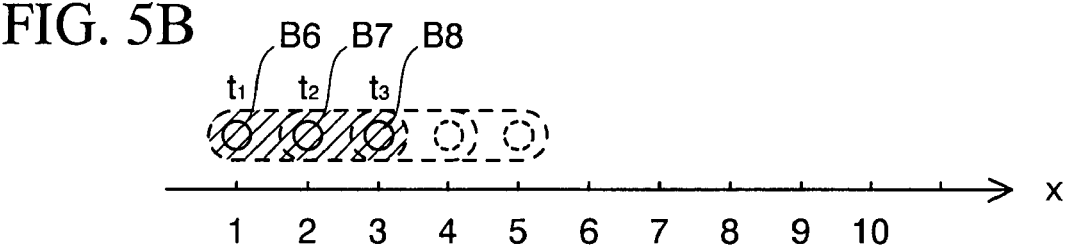

FIGS. 5A and 5B is a view for explaining a model of the spread of the electron beam in the scanning direction when the electron beam passes the measurement point of x=1 at time t1. Here, the electron beam is assumed to be composed of a unit electron beam having the size determined by the beam diameter, and the spread of the electron beam is assumed to be equal to a distance that the unit electron beam advances for 2 unit time periods.

FIG. 5A shows the case of low magnification which indicates that the electron beam spreads and irradiates for 5 unit distance that is equivalent to a distance encompassing 5 pieces of unit electron beams (B1, B2, B3, B4, and B5). The electron beam in this spread range is equivalent to an "electron beam spreading in the scanning direction from the measurement point to a distance depending on a scanning speed". This electron beam will be hereinafter referred to as an "extended electron beam". FIG. 5B shows the case of high magnification in which the extended electron beam spreads for 3 unit distance that is equivalent to a distance encompassing 3 pieces of unit electron beams (B6, B7, and B8).

Figure 6A:
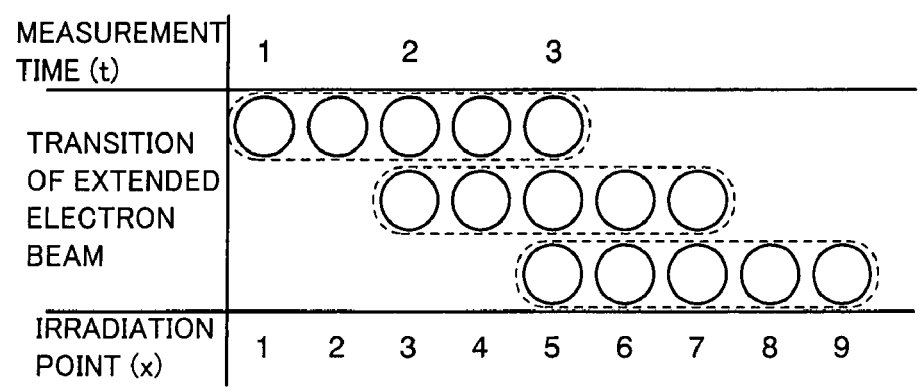
FIGS. 6A and 6B are first diagrams for explaining an electron beam intensity distribution adjusting process.
Figure 6B:
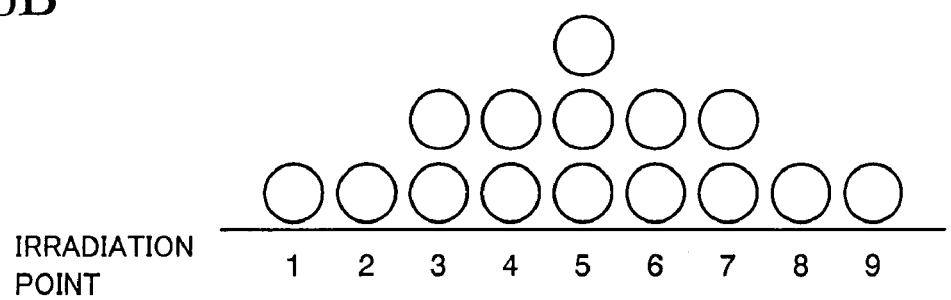

FIGS. 6A and 6B are diagrams showing the electron beam intensity distribution in the case of measurement with three measurement points, i.e., at the measurement time t1 to 3. FIG. 6A schematically shows the continuously traveling electron beam in the form of discrete transition of the extended electron beam. Here, the first row of transition of the extended electron beam represents the electron beam irradiated on the sample at a certain time (t=1), while the second row represents the electron beam irradiated on the sample when the electron beam travels at a lapse of a certain short time from the time of the first row. Similarly, the third row represents the electron beam irradiated on the sample when the electron beam travels at a lapse of the certain short time from the time of the second row.

FIG. 6B shows the electron beam intensity distribution obtained by summing up the quantity of electron beam for each unit distance. As shown in the drawing, when there are three measurement points, the distance in the scanning direction of the irradiation of the electron beam covers the irradiation points having the coordinate values from 1 to 9. Moreover, the drawing shows that the quantity of electron beam is equal to 3 at the irradiation point 5.

(2) Adjustment of Electron Beam Intensity Distribution

Assuming that the electron beam intensity distribution obtained in FIGS. 6A and 6B is defined as standard electron beam intensity distribution, a process to adjust the electron beam intensity distribution obtained at the magnification of observation different from that used in FIGS. 6A and 6B will be described below. Note that the electron beam intensity distribution in FIG. 6B is the same as the electron beam intensity distribution in FIG. 4A and that the standard effective irradiation travel distance SEID is equal to 3.46.

FIGS. 7A to 7C are diagrams showing transition of the extended electron beam when setting the magnification of observation applied hereto is set twice as large as the magnification of observation (defined as standard magnification) used for obtaining the standard electron beam intensity distribution.

As similar to FIG. 6A, FIG. 7A schematically shows the continuously traveling electron beam in the form of transition of the discrete extended electron beam. FIG. 7A applies the magnification of observation which is twice as large as that used in FIG. 6A. Accordingly, the coverage of the measurement points (the irradiation points) at each measurement time period is narrower as compared to FIG. 6A.

Figure 8:
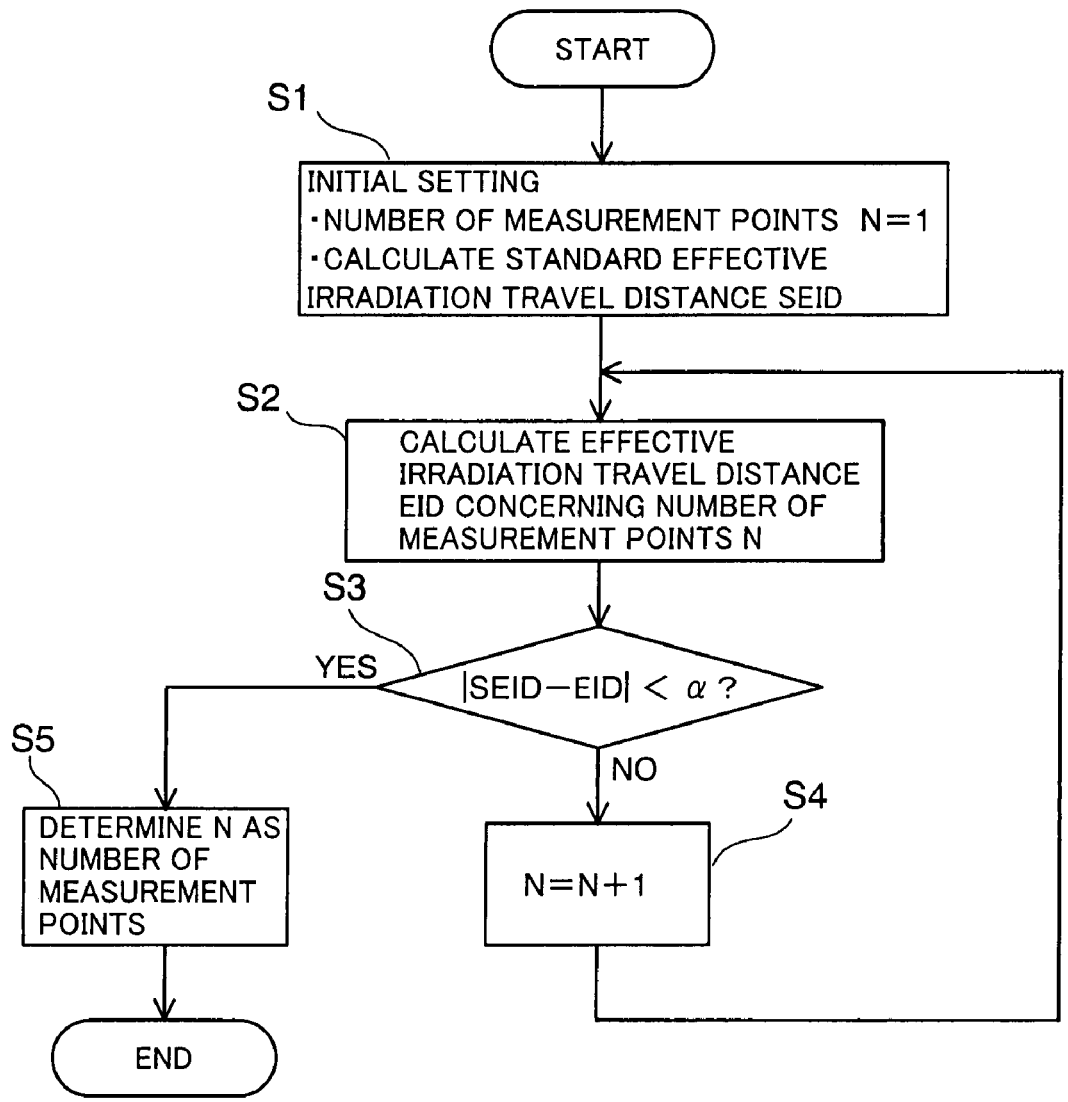
FIG. 8 is a flowchart showing an example of a process to determine the electron beam intensity distribution.

FIG. 8 is a flowchart showing a process to equalize the electron beam intensity distribution of FIGS. 7A to 7C to the standard electron beam intensity distribution.

First of all, initial setting is performed in step S1 in FIG. 8. In the initial setting, the number of measurement points N is set to 1. Moreover, the standard effective irradiation travel distance SEID is calculated in advance. Here, the electron beam intensity distribution shown in FIGS. 6A and 6B is defined as the standard electron beam intensity distribution and the standard effective irradiation travel distance SEID is equal to 3.46.

An effective irradiation travel distance EID when the number of measurement points is equal to N is calculated in the next step S2.

The effective irradiation travel distance EID is compared with the standard effective irradiation travel distance SEID in the next step S3. When an absolute value of the difference between the effective irradiation travel distance EID and the standard effective irradiation travel distance SEID is judged to be smaller than a predetermined value $\alpha$ (such as 0.2), the process goes to step S5 to determine the number of measurement points equal to N and then the process is completed. In contrast, the process goes to step S4 when the absolute value of the difference between the effective irradiation travel distance EID and the standard effective irradiation travel distance SEID is judged to be grater than the predetermined value $\alpha$.

The number of measurement points N is incremented by 1 in the next step S4 and then the process returns to step S2 to continue the process to calculate the number of measurement points.

FIG. 7B shows a calculation result when the number of measurement points is equal to 3. When the number of measurement points is equal to 3, the value of the electron beam intensity distribution is equal to 1.78 which is substantially different from the value of the standard electron beam intensity distribution.

FIG. 7C shows a calculation result when the number of measurement points is equal to 7. Here, the effective irradiation travel distance is close to the standard effective irradiation travel distance.

In this case, the number of measurement points is set to 7 when calculating the quantity of electrons of the measurement target. Specifically, a given operation (such as averaging) is performed with use of the quantity of electrons detected upon irradiation of the electron beam onto seven adjacent measurement points including a given measurement point, thereby determining the quantity of electrons in the relevant position. In this way, it is possible to substantially equalize the range of irradiation of the electron beam when the measurement object is observed by changing the magnification, and thereby to suppress fluctuation in the measurement data.

EXAMPLE 2

In Example 2, a method of equalizing two types of the electron beam intensity distribution when scanning with electron beams having mutually different beam diameters will be described.

FIGS. 9A to 9C are diagrams for explaining calculation of the electron beam intensity distribution when the distance of irradiation of the extended electron beam is expressed by 6 unit distance. Meanwhile, FIGS. 10A to 10C are diagrams for explaining a process to equalize the electron beam intensity distribution, which represents the case of using an electron beam having a larger beam diameter than a beam diameter in FIGS. 9A to 9C, to the electron beam intensity distribution shown in FIGS. 9A to 9C.

The distance of irradiation of the extended electron beam depends not only on the scanning speed of the electron beam but also on the beam diameter of the electron beam. For instance, a beam diameter of a standard electron beam is assumed to be expressed by a radius a while a beam diameter of a target electron beam is assumed to be expressed by a radius b (b>a). When the distance of irradiation of the extended electron beam is set equal to the 6 unit distance, the extended electron beam generated by the electron beam having the beam diameter of the radius b irradiates for a longer distance than the extended electron beam generated by the electron beam having the beam diameter of the radius a. To simplify calculation, the extended electron beam generated by the beam diameter of the radius b will also be expressed by use of the unit electron beam applied to the beam diameter of the radius a. For example, as shown in FIGS. 10A to 10C, the distance of irradiation of the extended electron beam will be set to 7 unit distance.

FIG. 9A schematically shows the continuously traveling electron beam in the form of transition of the discrete extended electron beam as similar to FIG. 6A.

FIG. 9A shows the electron beam intensity distribution when setting the number of measurement points equal to 3, and FIG. 9C is the view of finding the value of the electron beam intensity distribution obtained in FIG. 9B.

FIG. 10A schematically shows the continuously traveling electron beam in the form of transition of the discrete extended electron beam as similar to FIG. 9A.

Here, the standard effective irradiation travel distance is equal to 3.89 as shown in FIG. 9C. In contrast, the effective irradiation travel distance when setting the number of measurement points to 3 is equal to 4.19 as shown in FIG. 10B. As a result, if the number of measurement points is maintained at 3 points, the measurement value turns out to be different from the standard measurement value.

In this embodiment, the quantity of irradiated electron beam is adjusted by use of an adjustment coefficient in order to align the effective irradiation travel distance with the standard irradiation travel distance. This adjustment coefficient is the value for adjusting the quantity of irradiated electron beam of the extended electron beam. The effective irradiation travel distance is aligned with the standard irradiation travel distance by multiplying both ends of the extended electron beam forming the electron beam intensity distribution by this adjustment coefficient.

In this example, the value of the quantity of irradiated electron beam of the extended electron beam is reduced to bring the effective irradiation travel distance of 4.19 closer to the standard value of 3.89. As shown in FIG. 10C, the adjustment coefficient is calculated so as to make the effective irradiation travel distance equal to 3.89. In other words, the effective irradiation travel distance can be made equal to 3.89 by setting the quantities of irradiated electron beam in the beginning and in the end of the measurement point to 0.68 relative to 1 representing the standard.

The number of measurement points is calculated based on this adjustment coefficient. Specifically, concerning the electron beam intensity distribution obtained by synthesizing the extended electron beams C1, C2, and C3, the unit electron beam amounts constituting the C1 and C3 are multiplied by 0.68. The result of calculation is expressed by 0.68×1+1+0.68×1=2.36. Accordingly, it is known that the effective irradiation travel distance becomes equal to the standard effective irradiation travel distance of 3.89 by setting the number of measurement point to 2.36. As a result, in this case, the number of measurement points should be set to 2.36 for calculating the quantity of electrons of the measurement target. In this way, even when using a measurement device having a different electron beam diameter, it is possible to prevent fluctuation in the measurement data by performing the above-described adjustment because the irradiation range of the electron beam becomes substantially equal to the case of using the electron beam having the standard beam diameter.

Figure 11:
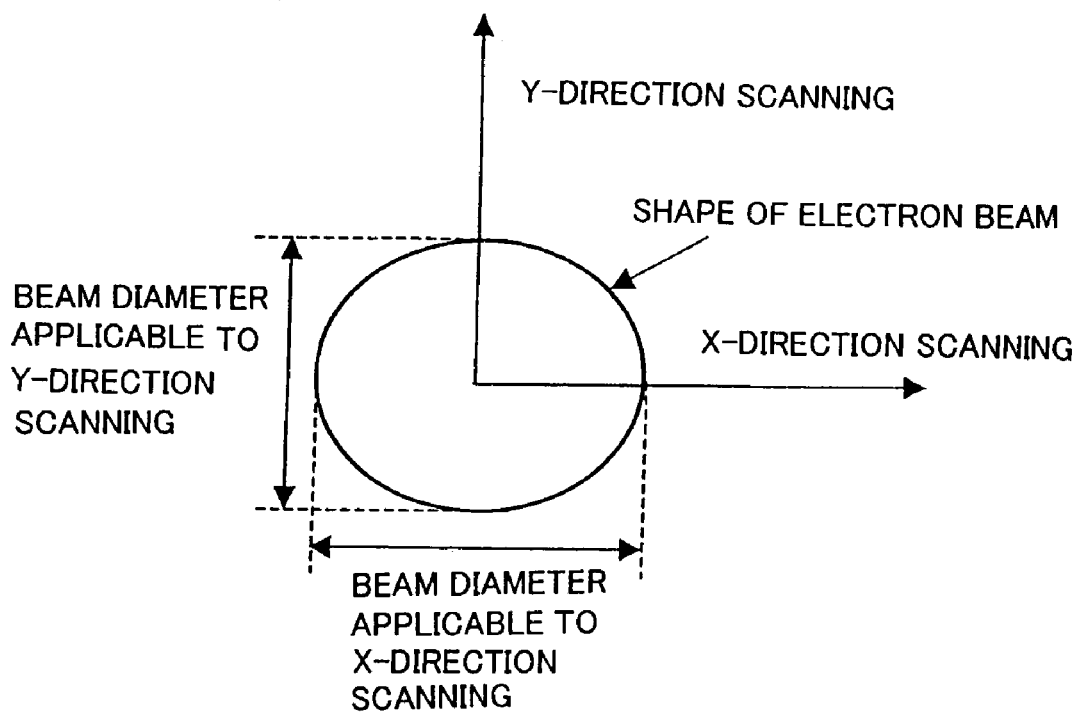
FIG. 11 is a view showing an example of a shape of an electron beam.

Meanwhile, regarding a difference in the diameter caused by changing the scanning direction in the case where the shape of the electron beam is not a perfect circle as shown in FIG. 11, it is possible to prevent fluctuation in the measurement data attributable to the different scanning directions by performing adjustment similar to this example.

Here, the control unit 20 of the scanning electron microscope 100 is formed of a microcomputer, for example, and the above-described process to adjust the number of measurement points is executed by using a program stored in the control unit 20 of the scanning electron microscope 100.

Moreover, the above-described adjustment of the electron beam intensity distribution may be executed at the time of generating the electron beam intensity distribution while regarding a quantity of secondary electrons at an irradiation point in a secondary electron intensity distribution image obtained by electron beam scanning as the quantity of electron beam.

(Line-Width Measurement)

Now, line-width measurement using the method of achieving the constant electron beam intensity distribution while resealing the magnification of observation will be described below with reference to flowcharts in FIG. 12 and FIG. 13.

Figure 12:
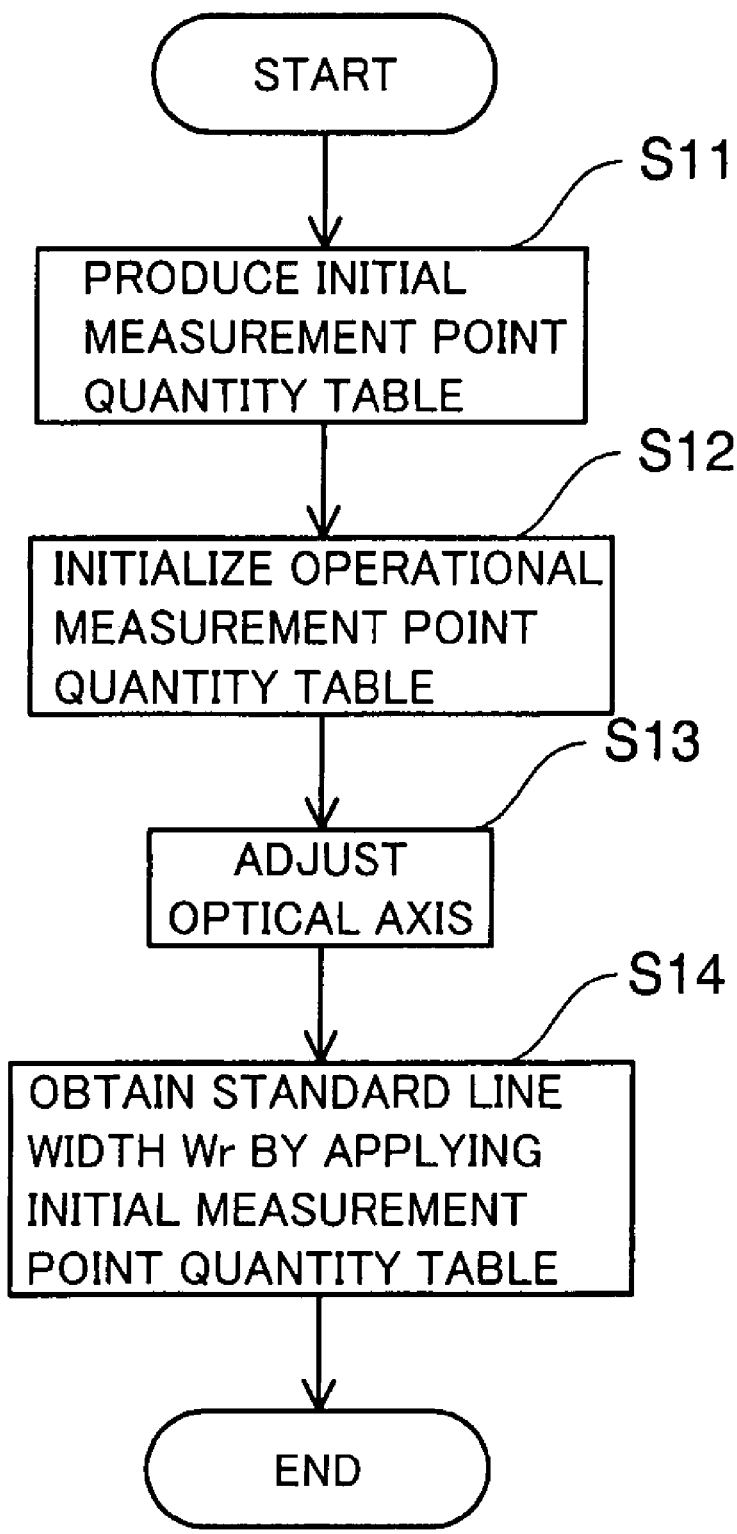
FIG. 12 is a flowchart showing an example of a process to determine an operation standard value in line-width measurement.
Figure 13:
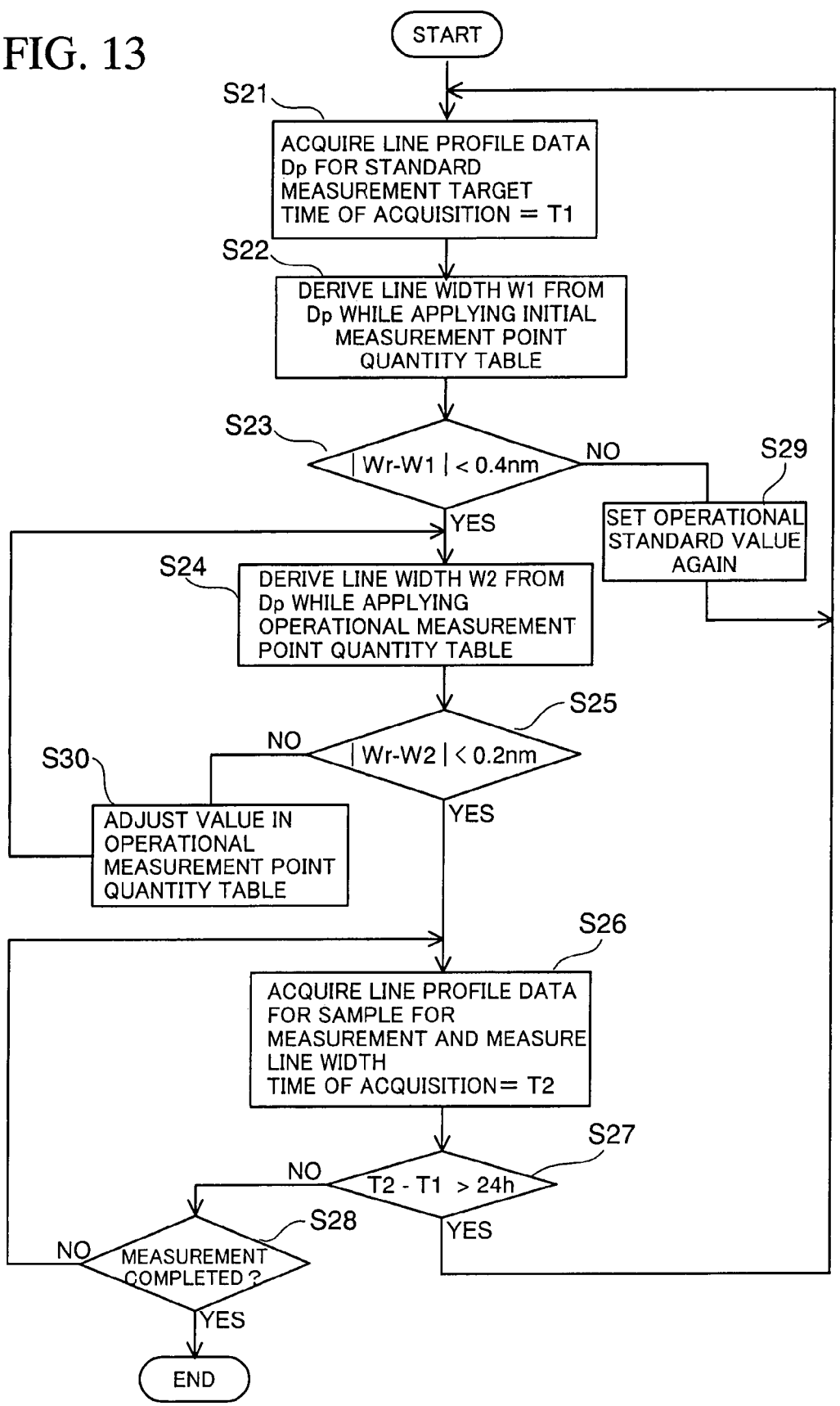
FIG. 13 is a flowchart showing an example of a process to execute the line-width measurement.

FIG. 12 shows a process flow for determining an operation standard value and FIG. 13 shows a process flow for performing the line-width measurement.

Before measuring the line width by use of the scanning electron microscope 100, the operation standard value is determined in accordance with the flowchart in FIG. 12.

First, an initial measurement point quantity table is produced in step S11. As shown in FIG. 14A, the initial measurement point quantity table defines the number of measurement points at respective magnification factors used in the scanning electron microscope 100. Determination of the number of measurement points is executed by use of the method described in this embodiment.

In the next step S12, the initial measurement point quantity obtained in step S11 as an operational measurement point quantity used in the line-width measurement. FIG. 14B shows an example of an operational measurement point quantity table.

An optical axis of the scanning electron microscope 100 is adjusted in the next step S13.

A standard line width Wr is obtained in the next step S14. The standard line width Wr is used as a standard for determining as to whether or not the scanning electron microscope functions normally at the time of actual line-width measurement. The standard line width Wr is determined by measuring a standard measurement target at predetermined standard magnification (such as a magnification factor of 50,000) while using the initial measurement point quantity table. FIG. 14C shows an example of a standard line width table. FIG. 14C shows that the standard line width Wr obtained at the magnification factor of 50,000 is equal to 210 nm.

Now, an actual process to measure the line width will be described below with reference to FIG. 13.

First, in step S21, a line profile data Dp representing a surface condition of a sample at the standard magnification are acquired by with use of the standard measurement target used for determination of the operational standard value. The time of acquisition of the line profile data Dp will be defined as T1.

In the next step S22, a line width W1 is derived from the line profile data Dp acquired in step S21 while using the initial measurement point quantity table.

In the next step S23, the line width W1 obtained in step S22 is compared with the standard line width Wr. Specifically, the standard measurement target is measured at the standard magnification and the line width is determined by using the initial measurement points. Then, the judgment is made as to whether or not the line width falls within a predetermined acceptable error range. The predetermined acceptable error range is defined as a difference in the line width within 0.4 nm, for example. If the line width does not fall within the predetermined acceptable error range, the line width cannot be used as the standard value. In this case, the process goes to step S29 and the operational standard value is set up again. When the line width is judged to be within the predetermined acceptable error range, the process goes to step S24.

In the next step S24, a line width W2 is derived from the line profile data Dp while using the operational measurement point quantity table.

In the next step S25, the line width W2 is compared with the standard line width Wr and a judgment is made as to whether or not a difference between the line width W2 and the standard line width Wr falls within another predetermined acceptable error range. This predetermined acceptable error range is defined as a difference in the line width within 0.2 nm, for example. The process goes to step S26 when the line width falls within the predetermined acceptable error range or the process goes to step 30 when the line width does not fall within the predetermined acceptable error range.

In the next step S26, the line profile data for the sample for measurement are acquired and the line width is measured by use of the operational measurement point quantity table. Here, the time of acquisition of the line profile data will be defined as T2.

In the next step S27, the time period from the point of starting the operation to the point of measuring the sample for measurement is counted and a judgment is made as to whether or not the measured time period is longer than a predetermined period of time such as 24 hours. When the time period is shorter than 24 hours, the process goes to step S28. When the time period is longer than 24 hours, it is very likely that the condition of the sample has been changed. Accordingly, the process returns to step S21 and the operational standard value is set up again.

In the next step S28, a judgment is made as to whether or not the entire measurement of the line width is completed. When the entire measurement is completed, the process is terminated. The judgment of completion of the line-width measurement may be determined by presence of a notice for completion of the measurement to be issued by a user operating a button or the like. If the line-width measurement is not completed, then the process returns to step S26 to continue the measurement.

When the line width W2 determined by use of the operational measurement point quantity table does not fall within the acceptable error range as a result of comparison with the standard value in step S25, the process goes to step S30.

The value on the operational measurement quantity table is adjusted in step S30. Since the operational standard value has been proved to be applicable in step S23, the number of operational measurement points is slightly adjusted to an applicable value in step S30. For example, if the line width W2 is greater than the standard line width Wr, the number of measurement points at the same magnification as the standard magnification is decremented by 0.1. On the other hand, if the line width W2 is smaller than the standard line width Wr, the number of measurement points at the same magnification as the standard magnification is incremented by 0.1. Regarding the magnification other than the standard magnification, the number of measurement points is derived from the number of measurement points at the standard magnification in accordance with the method described in this embodiment.

Although the number of measurement points is adjusted by incrementing or decrementing 0.1 in the above description, the pitch of such increment or decrement is not limited only to this value. Moreover, although the allowable time lapse of the sample is set within 24 hours for avoiding the condition change in step S27, this allowance can also be changed as appropriate. Furthermore, the acceptable error range can also be changed as appropriate.

As described above, when resealing the magnification of observation and thereby changing the scanning travel distance per unit time, the electron beam intensity distribution is adjusted so as to equalize the electron beam intensity distribution representing the distribution of the electron beam irradiated for each value of the scanning travel distance. In this way, even when the line width is measured while resealing the magnification of observation, the distance of the electron beam irradiation in the scanning direction becomes substantially equal to the standard distance. Consequently, it is possible to prevent fluctuation in the measurement result of the line width.

Moreover, when the beam diameters of the electron beams are different despite the same magnification of observation due to use of different scanning electron microscopes, the distances of irradiation of the electron beams are equalized to the standard distance by adjusting the electron beam intensity distribution. Accordingly, it is possible to prevent different measurement results between the scanning electron microscopes in terms of the same line width of the pattern.

In addition, when the beam diameter of the electron beam is different depending on the scanning direction in spite of using the same scanning electron microscope, the distance of irradiation of the electron beam is equalized to the standard distance by adjusting the electron beam intensity distribution. Accordingly, it is possible to prevent different measurement results from arising depending on the scanning direction for the same line width of the pattern.

In this way, even when measuring the line width lower magnification of observation while defining a wider range of the sample as a measurement target, it is possible to obtain the same value as a result of measurement at higher magnification. Accordingly, it is possible to measure a wide range more of the sample more efficiently.

What is claimed is:

1. A line-width measurement adjusting method, which is used when first and second electron beam intensity distributions for measuring a line width are produced from intensity distribution images of secondary electrons obtained respectively by scanning a first irradiation surface distance with an electron beam at first magnification, and by scanning a second irradiation surface distance with an electron beam at second magnification, the line-width measurement adjusting method comprising the step of adjusting the second electron beam intensity distribution of the electron beam at the second magnification such that the second electron beam intensity distribution is equal to the first electron beam intensity distribution of the electron beam at the first magnification;

wherein the electron beam intensity distribution is expressed by an amount of electron beam per unit distance assuming that the amount of electron beam is measured for each unit distance in a scanning direction by scanning with the electron beam, and wherein a value of the electron beam intensity distribution is obtained by firstly dividing the electron beam intensity distribution in half in the scanning direction, that is, into a primary electron beam intensity distribution and a secondary electron beam intensity distribution, and by then finding a difference in distance between a center of mass of the primary electron beam intensity distribution and a center of mass of the secondary electron beam intensity distribution.

2. A line-width measurement adjusting method, which is used when first and second electron beam intensity distributions for measuring a line width are produced from intensity distribution images of secondary electrons obtained respectively by scanning a first irradiation surface distance with an electron beam having a first beam diameter, and by scanning a second irradiation surface distance with an electron beam having a second beam diameter, the line-width measurement adjusting method comprising the step of adjusting the second electron beam intensity distribution of the electron beam having the second beam diameter such that the second electron beam intensity distribution is equal to the first electron beam intensity distribution of the electron beam having the first beam diameter;

wherein the electron beam intensity distribution is expressed by an amount of electron beam per unit distance assuming that the amount of electron beam is measured for each unit distance in a scanning direction by scanning with the electron beam, and a value of the electron beam intensity distribution is obtained by firstly dividing the electron beam intensity distribution in half in the scanning direction, that is, into a primary electron beam intensity distribution and a secondary electron beam intensity distribution, and by then finding a difference in distance between a center of mass of the primary electron beam intensity distribution and a center of mass of the secondary electron beam intensity distribution.

3. A line-width measurement adjusting method, which is used when first and second electron beam intensity distributions for measuring a line width are produced from intensity distribution images of secondary electrons obtained respectively by scanning a first irradiation surface distance with an electron beam in the first direction, and by scanning a second irradiation surface distance with an electron beam in the second direction, the line-width measurement adjusting method comprising the step of adjusting second electron beam intensity distribution of the electron beam scanning in the second direction such that the second electron beam intensity distribution is equal to the first electron beam intensity distribution of the electron beam in the first direction;

wherein the electron beam intensity distribution is expressed by an amount of electron beam per unit distance assuming that the amount of electron beam is measured for each unit distance in a scanning direction by scanning with the electron beam, and a value of the electron beam intensity distribution is obtained by firstly dividing the electron beam intensity distribution in half in the scanning direction, that is, into a primary electron beam intensity distribution and a secondary electron beam intensity distribution, and by then finding a difference in distance between a center of mass of the primary electron beam intensity distribution and a center of mass of the secondary electron beam intensity distribution.

4. The line-width measurement adjusting method according to any of claims 1 to 3, wherein the center of mass is calculated by an operational expression defined as $X_0 = \Sigma(X_i \times P_i)/\Sigma P_i$ where $X_0$ is the center of mass, $X_i$ is an irradiation point per unit distance, and $P_i$ is a quantity of electron beam irradiated on the irradiation point $X_i$.

5. The line-width measurement adjusting method according to any of claims 1 to 3, wherein the second electron beam intensity distribution is adjusted by increasing or decreasing the second irradiation surface distance when producing the electron beam intensity distribution.

6. A scanning electron microscope having an electron scanning unit, comprising:

an electron gun provided at an upper area of the electron scanning unit for irradiating an electron beam onto a surface of a sample;

a motion stage provided at a lower area of the electron scanning unit for mounting the sample and horizontally moving the sample to receive the electron beam;

an electron detection unit provided between the upper area and the lower area of the electron scanning unit for detecting electrons emitted from the sample upon irradiation of the electron beam; and a control unit electrically connected with the electron scanning unit and comprising a computer readable medium containing instructions that, when executed, cause the control unit to for adjust second electron beam intensity distribution of the electron beam at second magnification such that the second electron beam intensity distribution is equal to first electron beam intensity distribution of the electron beam at first magnification;

wherein the electron beam intensity distribution is expressed by an amount of electron beam per unit distance assuming that the amount of electron beam is measured for each unit distance in a scanning direction by scanning with the electron beam, and a value of the electron beam intensity distribution is obtained by firstly dividing the electron beam intensity distribution in half in the scanning direction, that is, into a primary electron beam intensity distribution and a secondary electron beam intensity distribution, and by then finding a difference in distance between a center of mass of the primary electron beam intensity distribution and a center of mass of the secondary electron beam intensity distribution.

7. A scanning electron microscope having an electron scanning unit, comprising:

an electron gun provided at an upper area of the electron scanning unit for irradiating an electron beam onto a surface of a sample;

a motion stage provided at a lower area of the electron scanning unit for mounting the sample and horizontally moving the sample to receive the electron beam;

an electron detection unit provided between the upper area and the lower area of the electron scanning unit for detecting electrons emitted from the sample upon irradiation of the electron beam; and a control unit electrically connected with the electron scanning unit and comprising a computer readable medium containing instructions that, when executed, cause the control unit to for adjust second electron beam intensity distribution of the electron beam having a second beam diameter such that the second electron beam intensity distribution is equal to first electron beam intensity distribution of the electron beam having a first beam diameter;

wherein the electron beam intensity distribution is expressed by an amount of electron beam per unit distance assuming that the amount of electron beam is measured for each unit distance in a scanning direction by scanning with the electron beam, and a value of the electron beam intensity distribution is obtained by firstly dividing the electron beam intensity distribution in half in the scanning direction, that is, into a primary electron beam intensity distribution and a secondary electron beam intensity distribution, and by then finding a difference in distance between a center of mass of the primary electron beam intensity distribution and a center of mass of the secondary electron beam intensity distribution.

8. The scanning electron microscope according to any of claims 6 to 7, wherein the control unit calculates the center of mass by an operational expression defined as $X_0 = \Sigma(X_i \times P_i)/\Sigma P_i$ where $X_0$ is the center of mass, $X_i$ is an irradiation point per unit distance, and $P_i$ is a quantity of electron beam irradiated on the irradiation point $X_i$.

9. The scanning electron microscope according to any of claims 6 to 7, wherein the control unit adjusts the second electron beam intensity distribution by increasing or decreasing the second irradiation surface distance when producing the electron beam intensity distribution.

* * * * *